United States Patent
Yamamoto

(10) Patent No.: US 8,453,671 B2
(45) Date of Patent: Jun. 4, 2013

(54) APPARATUS FOR CONTROLLING INTERNAL PRESSURE OF HERMETICALLY SEALED CHAMBER

(75) Inventor: Kanjun Yamamoto, Kanazawa (JP)

(73) Assignee: Shibuya Kogyo Co., Ltd., Kanazawa-shi, Ishikawa (JP)

( * ) Notice: Subject to any disclaimer, the term of this patent is extended or adjusted under 35 U.S.C. 154(b) by 0 days.

(21) Appl. No.: 13/066,815

(22) Filed: Apr. 26, 2011

(65) Prior Publication Data
US 2011/0265894 A1 Nov. 3, 2011

(30) Foreign Application Priority Data
Apr. 30, 2010 (JP) ................. 2010-105543

(51) Int. Cl.
*A61L 2/00* (2006.01)
(52) U.S. Cl.
USPC ......... 137/487.5; 137/545; 422/292; 422/295
(58) Field of Classification Search
USPC ..... 137/544, 545; 422/292, 295, 296; 138/26, 138/30; 60/469
See application file for complete search history.

(56) References Cited

U.S. PATENT DOCUMENTS

| | | | | |
|---|---|---|---|---|
| 2,896,566 A | * | 7/1959 | Laurie, Jr. et al. | 116/34 R |
| 3,384,914 A | * | 5/1968 | Wilhelmsen | 15/1.7 |
| 3,633,946 A | * | 1/1972 | Kazmierski, Jr. | 285/229 |
| 3,672,398 A | * | 6/1972 | Ichiryu et al. | 137/565.34 |
| 4,456,038 A | * | 6/1984 | Gwaltney et al. | 141/95 |
| 4,694,409 A | * | 9/1987 | Lehman | 700/282 |
| 4,702,287 A | * | 10/1987 | Higbie et al. | 141/4 |
| 5,020,564 A | * | 6/1991 | Thoman et al. | 137/102 |
| 5,816,046 A | * | 10/1998 | Paeth et al. | 60/469 |

FOREIGN PATENT DOCUMENTS

| | | | |
|---|---|---|---|
| JP | 2001340432 A | * | 12/2001 |
| JP | 2002-301138 | | 10/2002 |

OTHER PUBLICATIONS

Patent Translation, Kazuhito, JP 2002301138, Oct. 15, 2002.*
Patent Translation, Tanitsu, JP 2001340432, Dec. 11, 2001.*

* cited by examiner

*Primary Examiner* — Stephen M Hepperle
*Assistant Examiner* — Angelisa Hicks
(74) *Attorney, Agent, or Firm* — Flynn, Thiel, Boutell & Tanis, P.C.

(57) ABSTRACT

An apparatus for controlling an internal pressure of a hermetically sealed chamber at a prescribed pressure level serves to relax pressure changes in the hermetically sealed chamber. The chamber is connected to an inlet passage for supplying air from an external environment through an aseptic filter, an outlet passage for discharging a gas through an aseptic filter, and an inlet valve and an outlet valve for selectively opening and closing the inlet passage and the outlet passage, respectively. The apparatus also includes a controller for controlling the inlet valve and the outlet valve to keep the internal pressure of the chamber at a prescribed positive pressure level. An elastic membrane of silicone rubber which is expanded or retracted depending on a change in the internal pressure of the chamber to relax the pressure change is connected to the outlet passage between the aseptic filter and the outlet valve.

1 Claim, 4 Drawing Sheets

APPARATUS FOR CONTROLLING INTERNAL PRESSURE OF HERMETICALLY SEALED CHAMBER

BACKGROUND OF THE INVENTION

1. Field of the Invention

The present invention relates to an apparatus for controlling an internal pressure of a hermetically sealed chamber to maintain the internal pressure at a prescribed pressure level.

2. Description of the Related Art

There have widely been used apparatus with a hermetically sealed chamber, such as an aseptic filling machine for filling a container in an aseptic environment with a processor such as a filling machine or the like in an isolator (see Japanese laid-open patent publication No. 2002-301138). Specifically, Japanese laid-open patent publication No. 2002-301138 discloses an isolator system including an isolator serving as an isolating device which houses therein a production facility such as a powder filling machine and a sterilization casing serving as a pass box for sterilizing an object such as a raw material to be delivered to the powder filling machine and then carrying the sterilized object into the isolator.

The isolator has a hermetically sealable structure for fully blocking a direct influx of ambient air to provide therein a hermetically sealed environment, i.e., a hermetically sealed chamber, that is fully isolated from the external environment. After the isolator is decontaminated with a decontaminating gas such as a hydrogen peroxide vapor or the like introduced therein, the isolator regulates a rate at which air is sent thereinto through an inlet port equipped with an aseptic filter such as a HEPA filter and a rate at which air is discharged therefrom through an outlet port equipped with an aseptic filter such as a HEPA filter, thereby keeping a prescribed positive pressure in the isolator. While the isolator is in operation, therefore, it keeps an aseptic environment therein by preventing ambient air from directly flowing thereinto instead of through the aseptic filters. The sterilization casing also has a hermetically sealable structure for accommodating an object therein. After an object placed in the sterilization casing is decontaminated by a decontaminating gas supplied to the sterilization casing, a joint between the sterilization casing and the isolator is opened and the object is delivered from the sterilization casing into the isolator. It is desirable to keep a prescribed positive pressure in the sterilization casing in the same manner as with the isolator. In recent years, it has been customary to keep a prescribed positive pressure in the sterilization casing by regulating a rate at which air is sent thereinto and a rate at which air is discharged therefrom.

If the internal pressure of the isolator and the sterilization casing is kept at an excessively high pressure level, then they need to have a hermetically sealed structure strong enough to withstand the high pressure. Therefore, it is the usual practice to keep a positive pressure slightly higher than the atmospheric pressure of the external environment, in the isolator and the sterilization casing.

After an object is placed in the sterilization casing, i.e., a hermetically sealed chamber, the sterilization casing is supplied with a hydrogen peroxide vapor to decontaminate the object. At this time, the internal pressure of the sterilization casing may quickly rise beyond the upper limit of an allowable positive pressure range for the sterilization casing. If the internal pressure of the sterilization casing is about to increase beyond the upper limit of the allowable positive pressure range, then a discharge valve connected to the sterilization casing is opened to lower the internal pressure. However, since the gas in the sterilization casing is discharged therefrom at this time, the introduced hydrogen peroxide vapor is also discharged, failing to decontaminate the object. Another problem is that if the introduced hydrogen peroxide vapor causes an abrupt internal pressure buildup in the sterilization casing, then the internal pressure of the sterilization casing may become uncontrollable. These problems manifest themselves particularly with containers having relatively small volumes, such as sterilization casings (decontamination casings) and pass boxes.

When the hydrogen peroxide vapor introduced into the hermetically sealed chamber is subsequently condensed in the decontamination process, the internal pressure of the hermetically sealed chamber may sharply drop below the lower limit of the allowable positive pressure range. If the internal pressure of the hermetically sealed chamber is going to drop below the lower limit of the allowable positive pressure range, then air is introduced into the hermetically sealed chamber to increase the internal pressure into the allowable positive pressure range. However, the introduced air reduces the density of the hydrogen peroxide vapor in the hermetically sealed chamber, so that the hydrogen peroxide vapor tends to fail to decontaminate the object. In the event that an abrupt internal pressure drop occurs in the hermetically sealed chamber, the internal pressure of the sterilization casing may become uncontrollable. These problems manifest themselves particularly with containers having relatively small volumes, such as sterilization casings (decontamination casings) and pass boxes.

SUMMARY OF THE INVENTION

It is an object of the present invention to provide an apparatus for controlling an internal pressure of a hermetically sealed chamber to prevent the internal pressure from changing abruptly.

According to a first aspect of the present invention, there is provided an apparatus for controlling an internal pressure of a hermetically sealed chamber at a prescribed pressure level, comprising an inlet passage connected to an external environment through an aseptic filter, for supplying air to the hermetically sealed chamber, an outlet passage connected to the external environment through an aseptic filter, for discharging a gas from the hermetically sealed chamber, an inlet valve for selectively opening and closing the inlet passage, an outlet valve for selectively opening and closing the outlet passage, a controller for controlling the inlet valve and the outlet valve to control an internal pressure of the hermetically sealed chamber, and pressure relaxing means connected to the outlet passage between the hermetically sealed chamber and the outlet valve, for relaxing abrupt pressure changes in the hermetically sealed chamber.

With the above arrangement, the density of a decontaminating medium introduced into the hermetically sealed chamber is prevented from being lowered, and hence the ability of the decontaminating medium to decontaminate the internal space of the hermetically sealed chamber is prevented from being lowered. In addition, the internal pressure of the hermetically sealed chamber is prevented from abruptly changing to an uncontrollable level.

According to a second aspect of the present invention, in the first aspect referred to above, the outlet passage include an outlet duct, and the pressure relaxing means comprises an elastic member disposed in the outlet duct.

According to a third aspect of the present invention, in the first aspect referred to above, the outlet passage include an outlet duct, and the outlet passage include a gas storage container connected to the outlet duct.

According to a fourth aspect of the present invention, the apparatus according to the third aspect referred to above further comprises a pressure-activated valve, the outlet duct and the gas storage container being connected to each other by the pressure-activated valve, wherein the pressure-activated valve is opened when the internal pressure of the hermetically sealed chamber increases beyond an upper limit of an allowable pressure range, and is closed when the internal pressure of the hermetically sealed chamber drops below a lower limit of the allowable pressure range.

According to a fifth aspect of the present invention, in the third aspect referred to above, the gas storage container includes a cylinder and a piston movable in the cylinder, and wherein when the internal pressure of the hermetically sealed chamber increases beyond an upper limit of an allowable pressure range, the piston is moved in the cylinder to relax an increase in the internal pressure of the hermetically sealed chamber, and when the internal pressure of the hermetically sealed chamber drops below a lower limit of the allowable pressure range, the piston is moved back in the cylinder to relax a reduction in the internal pressure of the hermetically sealed chamber.

According to a sixth aspect of the present invention, in the first aspect referred to above, the hermetically sealed chamber comprises a pass box connected to an isolator which is isolated from the external environment and kept aseptic therein, the pass box including an inlet port for introducing a decontaminating medium vapor therethrough into the pass box, wherein the decontaminating medium vapor is introduced through the inlet port into the pass box while the pass box is being hermetically sealed.

The above and other objects, features, and advantages of the present invention will become apparent from the following description when taken in conjunction with the accompanying drawings which illustrate preferred embodiments of the present invention by way of example.

DETAILED DESCRIPTION OF THE PREFERRED EMBODIMENTS

Figure 1:
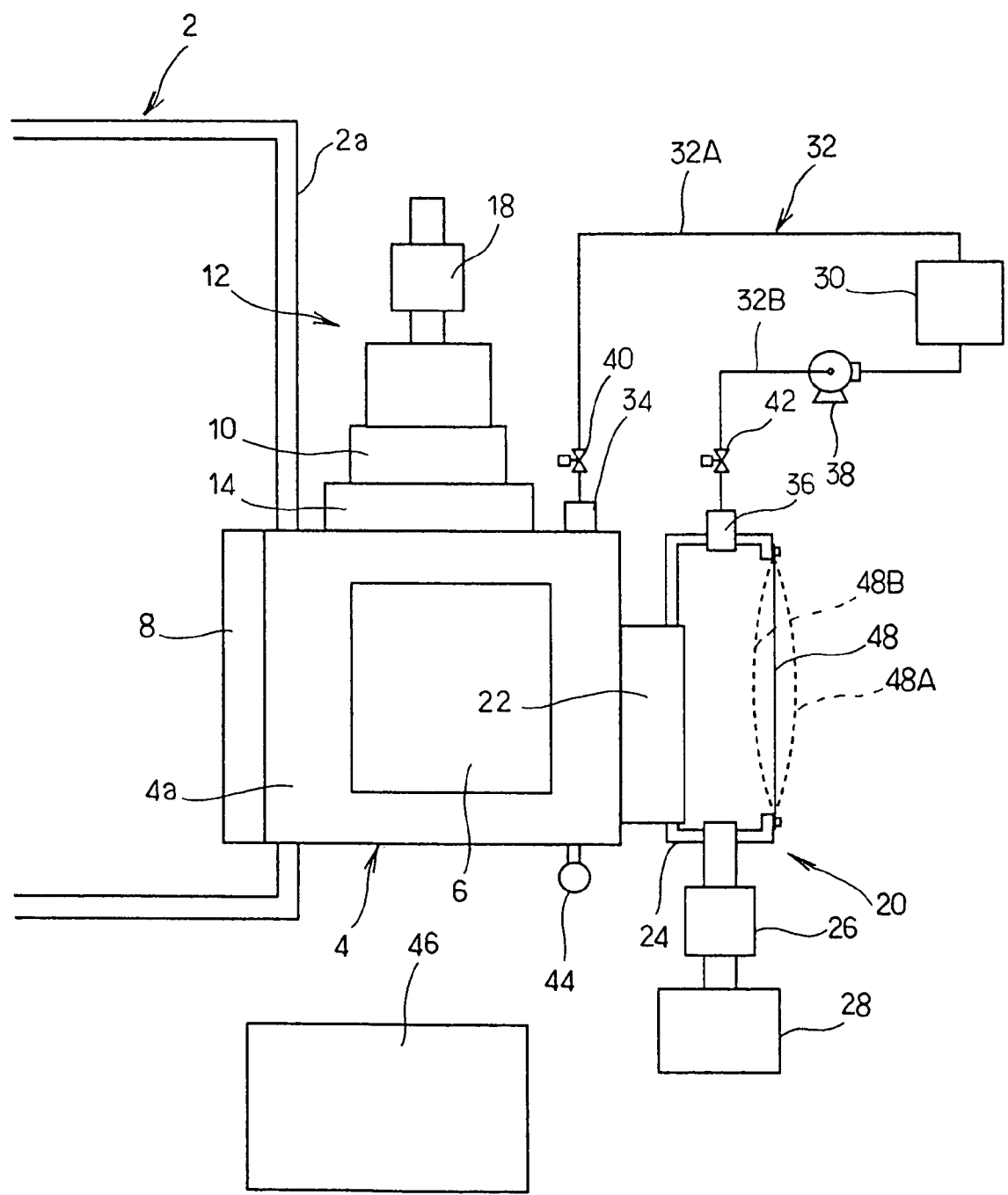
FIG. 1 is a schematic view of an apparatus for controlling an internal pressure of a hermetically sealed chamber according to a first embodiment of the present invention.

FIG. 1 schematically shows an apparatus for controlling an internal pressure of a hermetically sealed chamber according to a first embodiment of the present invention. As shown in FIG. 1, the apparatus is combined with an isolator 2 which has a hermetically sealable structure for fully blocking a direct influx of ambient air to provide therein a hermetically sealed environment, i.e., a hermetically sealed chamber, that is fully isolated from the external environment.

The isolator 2 has a sidewall 2a to which there is connected a pass box 4 serving as a hermetically sealed chamber. As with the isolator 2, the pass box 4 also has a hermetically sealable structure for fully blocking a direct influx of ambient air to provide therein a hermetically sealed environment, i.e., a hermetically sealed chamber, that is fully isolated from the external environment. The pass box 4 has an external door 6 mounted on a wall 4a thereof which is positioned outside of the isolator 2. When the external door 6 is open, it allows an object to be loaded into and out of the pass box 4. The pass box 4 also has an internal door 8 mounted on a section thereof which is positioned within the isolator 2. When the internal door 8 is open, it allows an object to be delivered from the pass box 4 into the isolator 2 and also allows an object to a delivered from the isolator 2 into the pass box 4. When the internal door 8 is open, it also keeps the internal spaces of the isolator 2 and the pass box 4 joined to each other while being fully isolated from the external environment by the external door 6 as it is closed.

The pass box 4 includes an inlet passage 12 which introduces ambient air into the hermetically sealed chamber of the pass box 4 when an intake fan 10 is actuated. The inlet passage 12 has a supply port connected to the hermetically sealed chamber of the pass box 4 and equipped with an aseptic filter 14 such as a HEPA filter. When the aseptic filter 14 cleans the supplied ambient air and introduces the cleaned ambient air as aseptic air into the hermetically sealed chamber of the pass box 4. The inlet passage 12 is connected to the external environment when an inlet valve 18 is opened, and is disconnected from the external environment when the inlet valve 18 is closed.

An outlet passage 20 is connected to the pass box 4 for discharging a gas therefrom. The outlet passage 20 includes an outlet duct 24 which is connected to the pass box 4 through an aseptic filter 22 such as a HEPA filter. The outlet passage 20 is connected to the external environment when an outlet valve 26 is opened, and is disconnected from the external environment when the outlet valve 26 is closed. A catalyst 28 is connected to the outlet valve 26 downstream thereof with respect to the direction in which a gas is discharged through the outlet passage 20 into the external environment. As described later, the gas discharged through outlet passage 20 may contain a decontaminating medium such as hydrogen peroxide or the like. When the gas is charged through the catalyst 28, such a decontaminating medium such as hydrogen peroxide or the like contained in the gas is decomposed by the catalyst 28.

A hydrogen peroxide vapor generator 30 for generating and supplying a hydrogen peroxide vapor to decontaminate the internal space of the pass box 4 is connected to the pass box 4. The hydrogen peroxide vapor generator 30 includes an inlet/outlet passage 32 having an inlet port 34 connected directly to the pass box 4 and an outlet port 36 connected to the outlet duct 24. The inlet/outlet passage 32 includes a supply passageway 32A extending from the hydrogen peroxide vapor generator 30 to the inlet port 34 and a discharge passageway 32B extending from the outlet port 36 to the hydrogen peroxide vapor generator 30. The supply passageway 32A and the discharge passageway 32B which are thus connected to the pass box 4 and the outlet duct 24, respectively, make up a circulation path for the hydrogen peroxide. The circulation path includes a blower 38 connected to the discharge passageway 32B, which, when actuated, supplies a hydrogen peroxide vapor generated by the hydrogen peroxide vapor generator 30 to the pass box 4 and discharges the hydrogen peroxide vapor from the pass box 4 through the outlet duct 24, so that the hydrogen peroxide vapor circulates through the circulation path. The supply passageway 32A has a supply valve 40 and the discharge passageway 32B has a discharge valve 42. When the supply valve 40 is open, it connects the supply passageway 32A to the inlet port 34.

When the discharge valve 42 is open, it connects the discharge passageway 32B to the outlet port 36. In the present embodiment, hydrogen peroxide vapor is used as the decontaminating medium for decontaminating objects in the pass box 4. However, any of various other decontaminating mediums may be used for decontaminating objects in the pass box 4.

The pass box 4 is combined with a pressure gage 44 for detecting the internal pressure of the pass box 4. A controller 46 controls the inlet valve 18, the intake fan 10, and the outlet valve 26 depending on the internal pressure of the pass box 4 as detected by the pressure gage 44. The outlet duct 24 of the outlet passage 20 includes a pressure-relaxing means 48 which comprises an elastic member. In the present embodiment, the pressure-relaxing means 48 comprises an elastic membrane 48 of a synthetic resin such as silicone rubber or the like which is mounted in an opening defined in a wall of the outlet duct 24. The pressure-relaxing means 48 serves to absorb and relax abrupt pressure changes in the pass box 4. Specifically, when the internal pressure of the pass box 4 rises, the elastic membrane 48 is expanded outwardly to a position 48A shown in FIG. 1. Conversely, when the internal pressure of the pass box 4 drops, the elastic membrane 48 is retracted inwardly to a position 48B shown in FIG. 1. It is possible for the pressure-relaxing means 48 to be directly mounted on the pass box 4. However, if the pressure relaxing means 48 is directly mounted on the pass box 4, the pass box 4 will possibly have its hermetically sealed state broken in the event of a leakage due to a rupture or pinhole of the elastic membrane 48. According to the present embodiment, an elastic membrane 48 is mounted in the internal space of the outlet duct 24 which is separate from the pass box 4 with the aseptic filter 22 interposed therebetween, so that a failure of the elastic membrane 48 will not adversely affect the internal environment of the pass box 4. The elastic membrane 48 is combined with the outlet duct 24, rather than with the inlet passage 12 because if the elastic membrane 48 is combined with the inlet passage 12, it will be expanded under the pressure of air flowing through the inlet passage 12.

Operation of the hermetically sealed chamber, i.e., the pass box 4, which is associated with the apparatus for controlling the internal pressure of the hermetically sealed chamber according to the first embodiment, will be described below.

The isolator 2 is periodically decontaminated therein. For decontaminating the internal space of the isolator 2, the internal door 8 of the pass box 4 is opened to join the internal spaces of the isolator 2 and the pass box 4 to each other. Then, the hydrogen peroxide vapor generator 30 generates and introduces a hydrogen peroxide vapor into the pass box 4 and the isolator 2, thereby decontaminating the internal space of the isolator 2. At this time, the supply valve 40 and the discharge valve 42 of the inlet/outlet passage 32 are opened, and the blower 38 is actuated to supply the hydrogen peroxide vapor generated by the hydrogen peroxide vapor generator 30 from the inlet port 34 to the pass box 4, introducing the hydrogen peroxide vapor into the pass box 4 and the isolator 2, and then discharge the hydrogen peroxide vapor through the aseptic filter 22 into the outlet duct 24, from which the hydrogen peroxide vapor flows through the outlet port 36 and the discharge passageway 32B back into the hydrogen peroxide vapor generator 30. In this manner, the hydrogen peroxide vapor is circulated through the circulation path.

The isolator 2 has an inlet system and an outlet system, not shown, for regulating a rate at which air is sent into the isolator 2 and a rate at which air is discharged from the isolator 2, thereby keeping a prescribed positive pressure in the isolator 2. While the isolator 2 is in operation, therefore, it keeps an aseptic environment therein by preventing ambient air from directly flowing thereinto. In the present embodiment, the internal spaces of the isolator 2 and the pass box 4 are decontaminated by the hydrogen peroxide vapor generated by the hydrogen peroxide vapor generator 30 which is associated with the pass box 4. However, the internal space of the isolator 2 may be decontaminated by a hydrogen peroxide vapor which is generated by another hydrogen peroxide vapor generator.

After the internal spaces of the isolator 2 and the pass box 4 are decontaminated, the internal door 8 is closed to isolate the internal spaces of the isolator 2 and the pass box 4 from each other. Then, the inlet passage 12 introduces ambient air through the aseptic filter 14 into the pass box 4, discharging a gas from the pass box 4 through the aseptic filter 22, the outlet passage 20, and the outlet valve 26. At this time, depending on the internal pressure of the pass box 4 as measured by the pressure gage 44, the controller 46 controls the intake fan 10, the inlet valve 18, and the outlet valve 26 to keep the internal pressure of the pass box 4 at a prescribed positive pressure level.

For introducing an object from the pass box 4 into the isolator 2, the internal door 8 is closed to isolate the internal spaces of the isolator 2 and the pass box 4 from each other. Then, the external door 6 is opened, and the object is inserted into the pass box 4. After the object is inserted into the pass box 4, the hydrogen peroxide vapor generator 30 generates and introduces a hydrogen peroxide vapor into the pass box 4 to decontaminate the internal space of the pass box 4 and the object placed in the pass box 4. When the hydrogen peroxide vapor is introduced into the hermetically sealed chamber of the pass box 4, the internal pressure of the pass box 4 rises. According to the present embodiment, the elastic membrane 48 that is mounted in the internal space of the outlet duct 24 which is connected to the pass box 4 through the aseptic filter 22 is expanded outwardly under the pressure buildup in the pass box 4, absorbing and relaxing abrupt pressure variations in the pass box 4. While the internal space of the pass box 4 and the object placed in the pass box 4 are being decontaminated as described above, the controller 46 keeps the internal pressure of the pass box 4 at a prescribed positive pressure level.

When the hydrogen peroxide vapor in the pass box 4 is subsequently condensed in the decontamination process, the internal pressure of the pass box 4 drops. At this time, the elastic membrane 48 is contracted inwardly, reducing the volume of the outlet duct 24 which is connected to the pass box 4 through the aseptic filter 22 thereby to make up for the reduction in the internal pressure of the pass box 4. As described above, when the internal pressure of the pass box 4 changes, the elastic membrane 48 is elastically deformed to absorb and relax the pressure change. Consequently, abrupt pressure changes in the pass box 4 are prevented from becoming uncontrollable, and the ability of decontaminate the internal space of the pass box 4 is prevented from being lowered due to supplied aseptic air or discharged gas. If the inlet valve 18 and the outlet valve 26 have too large of openings to be opened and closed with a desired response, then another inlet passage and another outlet passage may be provided for pressure control, and more responsive valves may be connected to those inlet and outlet passages. The aseptic filter 14 may be connected upstream of the inlet valve 18 with respect to the direction along which ambient air is supplied through the inlet passage 12.

Figure 2:
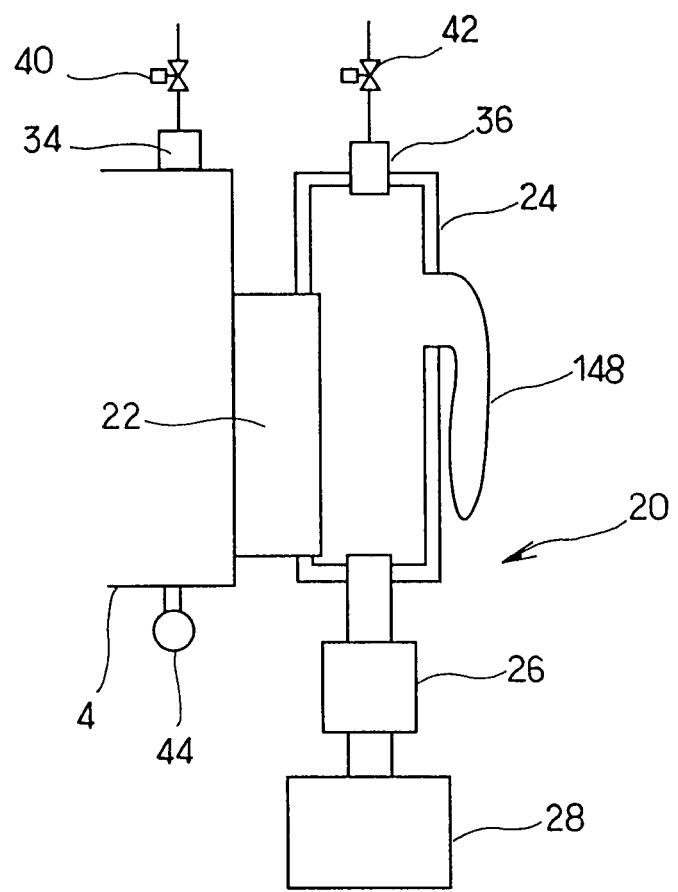
FIG. 2 is a schematic view of an apparatus for controlling an internal pressure of a hermetically sealed chamber according to a second embodiment of the present invention.

FIG. 2 schematically shows an apparatus for controlling an internal pressure of a hermetically sealed chamber according to a second embodiment of the present invention. As shown in FIG. 2, the apparatus for controlling the internal pressure of the hermetically sealed chamber according to the second embodiment includes an elastic pouch 148 of a synthetic resin such as silicone rubber or the like which serves as an elastic member of a pressure relaxing means. The elastic pouch 148 operates in the same manner and offers the same advantages as the elastic membrane 48 according to the first embodiment shown in FIG. 1. Those parts of the apparatus according to the second embodiment which are identical to those of the apparatus according to the first embodiment are denoted by identical reference characters, and will not be described in detail below.

Figure 3:
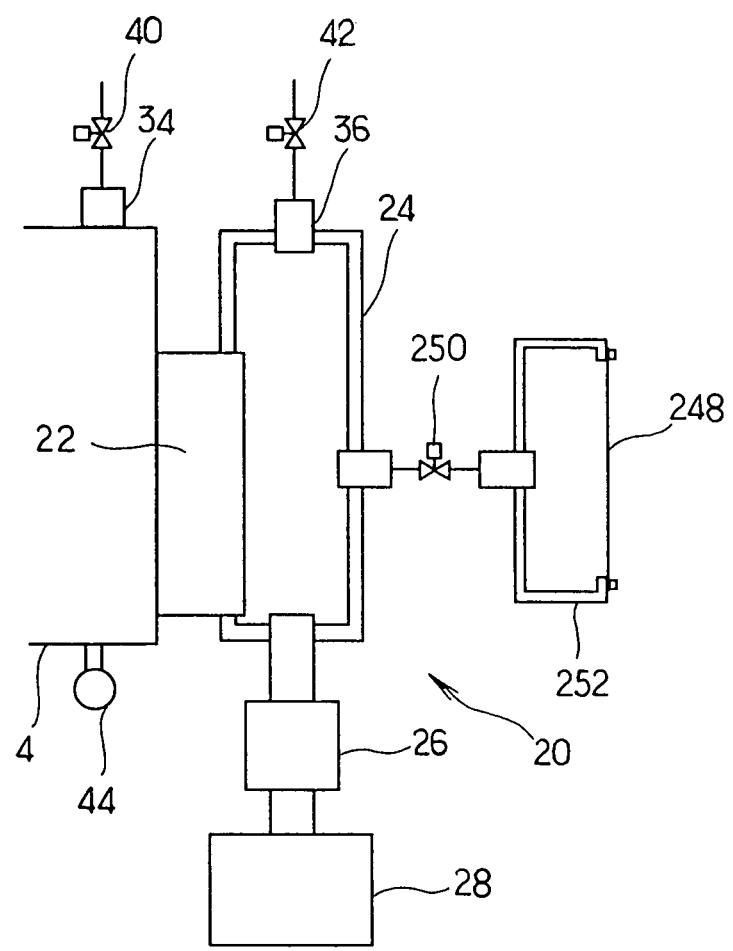
FIG. 3 is a schematic view of an apparatus for controlling an internal pressure of a hermetically sealed chamber according to a third embodiment of the present invention.

FIG. 3 schematically shows an apparatus for controlling an internal pressure of a hermetically sealed chamber according to a third embodiment of the present invention. As shown in FIG. 3, the apparatus for controlling the internal pressure of the hermetically sealed chamber according to the third embodiment includes a gas storage container 252 connected to the outlet duct 24 by a pressure-activated valve 250. The gas storage container 252 includes an elastic membrane 248 of a synthetic resin such as silicone rubber or the like which is the same as the elastic membrane 48 according to the first embodiment, for absorbing and relaxing abrupt pressure variations in the gas storage container 252. According to the present embodiment, when the internal pressure of the pass box 4 as measured by the pressure gage 4 exceeds the upper limit of the allowable pressure range, the valve 250 is opened to connect the outlet duct 24 to the gas storage container 252. Those parts of the apparatus according to the third embodiment which are identical to those of the apparatus according to the first embodiment are denoted by identical reference characters, and will not be described in detail below.

The apparatus for controlling the internal pressure of the hermetically sealed chamber according to the third embodiment operates as follows: When the pass box 4 is supplied with a hydrogen peroxide vapor and the internal pressure of the pass box 4 exceeds the upper limit of the allowable pressure range, the valve 250 is opened to connect the outlet duct 24 to the gas storage container 252. The internal pressure of the gas storage container 252 is substantially at an atmospheric pressure level. Therefore, the internal pressure of the pass box 4 which has increased beyond the atmospheric pressure is lowered to the atmospheric pressure level. In this manner, abrupt pressure buildups in the pass box 4 are absorbed and relaxed by the gas storage container 252 combined with the elastic membrane 248.

When the hydrogen peroxide vapor is subsequently condensed to lower the internal pressure of the pass box 4 below the lower limit of the allowable pressure range, the valve 250 is opened to connect the pass box 4 to the gas storage container 252. As the internal pressure of the gas storage container 252 is in an allowable pressure range higher than the atmospheric pressure, the internal pressure of the pass box 4 which has been lowered below the allowable pressure range increases back into the allowable pressure range. In this manner, abrupt pressure buildups in the pass box 4 are absorbed and relaxed by the gas storage container 252 combined with the elastic membrane 248. When the internal pressure of the pass box 4 settles in the allowable pressure range, the valve 252 is closed. The elastic membrane 248 operates in the same manner and offers the same advantages as the elastic membrane 48 according to the first embodiment shown in FIG. 1 and the elastic pouch 148 according to the second embodiment shown in FIG. 2.

Figure 4:
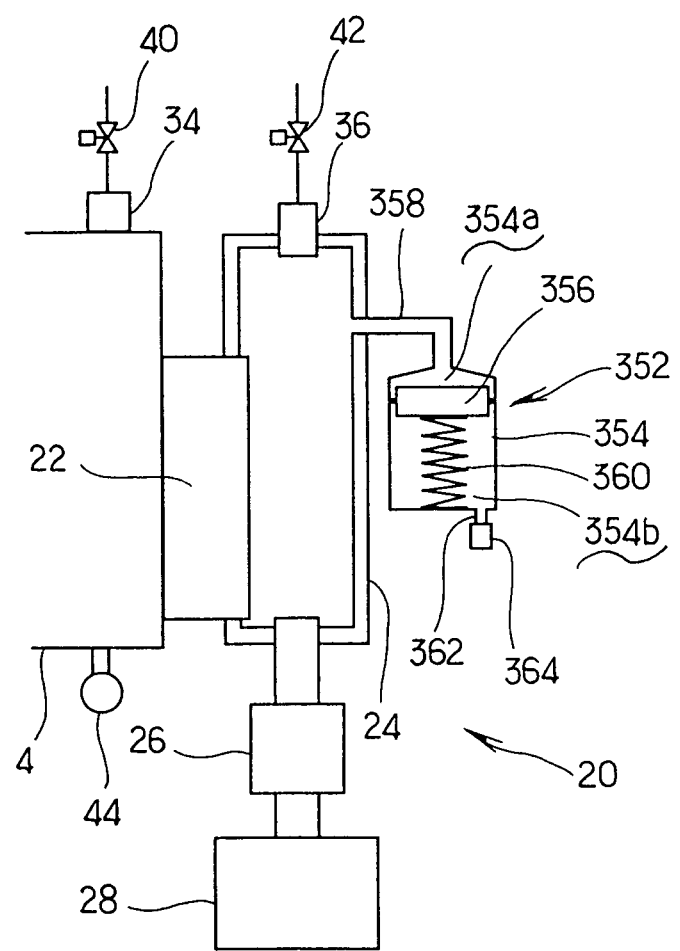
FIG. 4 is a schematic view of an apparatus for controlling an internal pressure of a hermetically sealed chamber according to a fourth embodiment of the present invention.

FIG. 4 schematically shows an apparatus for controlling an internal pressure of a hermetically sealed chamber according to a fourth embodiment of the present invention. As shown in FIG. 4, the apparatus for controlling the internal pressure of the hermetically sealed chamber according to the forth embodiment includes a gas storage container 352 having a cylinder 354 and a piston 356 movable therein. The gas storage container 352 is connected to the outlet duct 24 by a communication passage 358. The piston 356 divides the internal space of the cylinder 354 into a first cylinder chamber 354a connected to the pass box 4 and a second cylinder chamber 354b which houses therein a spring 360 for normally biasing the piston 356 into the first cylinder chamber 354a. The second cylinder chamber 354b has a discharge port 362 vented to the atmosphere for allowing the piston 356 to move smoothly in the cylinder 354. The discharge port 362 is connected to a catalyst 364 which prevents a hydrogen peroxide vapor leaked through a seal around the piston 356 from flowing out of the cylinder 354. Those parts of the apparatus according to the fourth embodiment which are identical to those of the apparatus according to the first embodiment are denoted by identical reference characters, and will not be described in detail below.

The apparatus for controlling the internal pressure of the hermetically sealed chamber according to the fourth embodiment operates as follows: When the internal pressure of the pass box 4 exceeds the upper limit of the allowable pressure range, the pressure buildup in the pass box 4 pushes the piston 356 against the bias of the spring 360, increasing the volume of the first cylinder chamber 354a to absorb and relax the pressure buildup in the pass box 4. When the internal pressure of the pass box 4 starts to drop, the piston 356 is pushed back under the bias of the spring 360, reducing the volume of the first cylinder chamber 354a to make up for the pressure drop in the pass box 4 below the lower limit of the allowable pressure range. The piston 356 may be moved by an actuator such as a motor, an air cylinder, or the like, rather than the spring 360, and the actuator may be operated depending on the pressure detected by the pressure gage 44 to expand or contract the first cylinder chamber 354a.

Although certain preferred embodiments of the present invention have been shown and described in detail, it should be understood that various changes and modifications may be made therein without departing from the scope of the appended claims.

What is claimed is:

1. An apparatus for controlling an internal pressure of a hermetically sealed chamber at a prescribed pressure level, comprising:

an inlet passage connected to an external environment through an inlet aseptic filter, for supplying air to said hermetically sealed chamber;

an outlet passage connected to the external environment through an outlet aseptic filter, for discharging a gas from said hermetically sealed chamber;

an inlet valve for selectively opening and closing said inlet passage;

an outlet valve for selectively opening and closing said outlet passage;

a controller for controlling said inlet valve and said outlet valve to control an internal pressure of said hermetically sealed chamber; and pressure relaxing means connected to said outlet passage between said hermetically sealed chamber and said outlet valve, for relaxing abrupt pressure changes in said hermetically sealed chamber, wherein said outlet passage includes an outlet duct, and said pressure relaxing means comprises an elastic member disposed in an internal space in said outlet duct which is separate from the hermetically sealed chamber with the outlet aspetic filter interposed therebetween.

* * * * *